(12) United States Patent
Marshall et al.

(10) Patent No.: US 11,472,829 B2
(45) Date of Patent: Oct. 18, 2022

(54) HEMICELLULOSE PROCESSING METHOD

(71) Applicant: Sappi Biotech UK Limited, Redcar (GB)

(72) Inventors: Edward Leslie Marshall, Redcar (GB); Alan Geoffrey Waite, Redcar (GB); David Peter Gibney, Redcar (GB)

(73) Assignee: SAPPI BIOTECH UK LIMITED, Redcar (GB)

( * ) Notice: Subject to any disclaimer, the term of this patent is extended or adjusted under 35 U.S.C. 154(b) by 0 days.

(21) Appl. No.: 16/487,926

(22) PCT Filed: Feb. 23, 2018

(86) PCT No.: PCT/GB2018/050474
§ 371 (c)(1),
(2) Date: Aug. 22, 2019

(87) PCT Pub. No.: WO2018/154314
PCT Pub. Date: Aug. 30, 2018

(65) Prior Publication Data
US 2019/0382431 A1    Dec. 19, 2019

(30) Foreign Application Priority Data

Feb. 23, 2017  (GB) ..................................... 1702892
Nov. 16, 2017  (GB) ..................................... 1718992

(51) Int. Cl.
| | |
|---|---|
| *C07G 1/00* | (2011.01) |
| *C07C 51/00* | (2006.01) |
| *C07C 59/08* | (2006.01) |
| *C07C 67/00* | (2006.01) |
| *C07C 69/12* | (2006.01) |
| *C08H 8/00* | (2010.01) |
| *C12P 7/10* | (2006.01) |
| *C12P 7/16* | (2006.01) |
| *C12P 19/02* | (2006.01) |
| *C12P 19/14* | (2006.01) |
| *C13K 13/00* | (2006.01) |

(52) U.S. Cl.
CPC ............... *C07G 1/00* (2013.01); *C07C 51/00* (2013.01); *C07C 59/08* (2013.01); *C07C 67/00* (2013.01); *C07C 69/12* (2013.01); *C08H 8/00* (2013.01); *C12P 7/10* (2013.01); *C12P 7/16* (2013.01); *C12P 19/02* (2013.01); *C12P 19/14* (2013.01); *C13K 13/002* (2013.01)

(58) Field of Classification Search
CPC ................................................. C08B 37/0057
See application file for complete search history.

(56) References Cited

U.S. PATENT DOCUMENTS

| | | | |
|---|---|---|---|
| 2010/0330633 A1 | 12/2010 | Walther et al. | |
| 2012/0285816 A1 | 11/2012 | Dauwel et al. | |
| 2013/0017585 A1* | 1/2013 | Ropars ..................... | C12P 7/16 435/150 |

FOREIGN PATENT DOCUMENTS

| | | |
|---|---|---|
| WO | 2014081848 A1 | 5/2014 |
| WO | 2014130352 A1 | 8/2014 |
| WO | 20151455534 A1 | 10/2015 |

OTHER PUBLICATIONS

Sluiter et al., "Determination of Sugars, Byproducts, and Degradation Products in Liquid Fraction Process Samples", National Renewable Energy Laboratory, Technical Report, NREL/TP-510-42623, Jan. 2008.
Sun, "Cereal Straw as a Resource for Sustainable Biomaterials and Biofuels", Chemistry, Extractives, Lignins, Hemicelluloses and Cellulose, Chapter 4, 2010.
International Search Report and Written Opinion pertaining to Application No. PCT/GB2018/050474 dated Feb. 23, 2017.
Search Report pertaining to Application No. GB17028922.9 dated Dec. 8, 2017.

* cited by examiner

*Primary Examiner* — Leigh C Maier
*Assistant Examiner* — Everett White
(74) *Attorney, Agent, or Firm* — Dinsmore & Shohl, LLP (57) ABSTRACT

A method of processing an aqueous hemicellulosic stream containing lignin, comprising: (a) contacting an aqueous hemicellulosic stream containing lignin with a $C_{3-8}$ alkyl alcohol at elevated temperature and acidic pH; (b) separating the reaction mixture obtained from step (a) into an aqueous phase containing hemicellulose-derived monosaccharide and an organic phase containing $C_{3-8}$ alkyl alcohol; (c) concentrating the organic phase obtained from step (b) to remove at least some $C_{3-8}$ alkyl alcohol; (d) treating the residue from step (c) with water or an aqueous medium having an alkaline pH; and (e) recovering $C_{3-8}$ alkyl alcohol from the product of step (d).

20 Claims, 4 Drawing Sheets

HEMICELLULOSE PROCESSING METHOD

FIELD OF THE INVENTION

The present invention relates to processing of lignocellulosic biomass. In particular, it relates to a method of processing a hemicellulosic stream which has been obtained from biomass.

BACKGROUND OF THE INVENTION

The three principal components of biomass are cellulose, lignin and hemicellulose, and they are present in almost all plant cell walls. The cellulosic material obtained from such biomass has a number of important industrial uses, notably in the production of paper from wood pulp. Accordingly a variety of processes have been developed for treating biomass to separate cellulosic material from other components of biomass, including the Kraft and sulfite processes. As well as producing cellulosic wood pulp, those processes also result in the production of by-products known as black liquor (Kraft process) or brown liquor (sulfite process) which typically contain hemicellulosic material together with lignin/lignin-derived products and inorganic chemicals. In recent times, demand for wood pulp containing higher cellulose content has been increasing, and processes for producing such forms of wood pulp (known as "dissolving pulp" or "dissolving cellulose") have been developed. Dissolving pulp finds use in the production of products such as rayon, viscose and cellophane. Typically in a process for producing dissolving pulp, an additional "pre-hydrolysis" stage is carried out in which lignocellulosic biomass is treated to remove hemicellulosic material and lignin/lignin-derived products, prior to subjecting the remainder of the cellulosic solids to further pulping conditions, such as Kraft conditions (treatment with an aqueous solution of sodium hydroxide and sodium sulphide at elevated temperature) or sulfite conditions (treatment with aqueous metal sulfite and/or bisulfite at elevated temperature). The separated hemicellulosic stream obtained from processes for producing dissolving pulp is typically referred to as "pre-hydrolysate liquor" or "pre-hydrolysis liquor", PHL, for a Kraft process and brown liquor (sometimes called red liquor, thick liquor, spent liquor or sulfite liquor) for a sulfite process.

Whilst the cellulosic material obtained from processes such as those outlined above is taken on and processed into various useful products, the hemicellulosic streams are often considered to be of little value and may be burnt or fed into a gasifier to recover their energy value.

A further, more recent, example of the use of cellulosic material as a feedstock in industrial processes is in the field of bioethanol production. Processes for the production of those biofuels from crop sources such as sugar beet and sweet sorghum have been developed and refined, and there has been a significant rate of growth in biofuel production in recent years. The use of hemicellulosic material as a feedstock for bioethanol production has also been investigated. However, the effectiveness of fermentation of hemicellulosic feedstocks is limited by the fact that unlike cellulosic feedstocks they contain a mixture of pentose and hexose sugars which is typically harder for microorganisms to utilise. Additionally, hemicellulosic feedstocks tend to contain acids, aldehydes, furan derivatives and lignin-derived products which can act to inhibit the effectiveness of fermentation-utilising processes.

WO 2015/155534 discloses a method of processing an aqueous hemicellulosic stream, comprising (a) contacting an aqueous hemicellulosic stream with a $C_{3-8}$ alkyl alcohol at elevated temperature and acidic pH to produce a reaction mixture comprising a $C_{3-8}$ alkyl ester and a hemicellulose-derived monosaccharide; and (b) separating the reaction mixture into an aqueous phase comprising said hemicellulose-derived monosaccharide and an organic phase comprising said $C_{3-8}$ alkyl ester.

In the process of WO 2015/155534 it is advantageous to recover $C_{3-8}$ alkyl alcohol at the end of the process. The organic phase obtained by reacting the feed stream contains this alcohol and $C_{3-8}$ alkyl esters, and it usually also contains lignin and other components, for example hemicellulose and hemicellulose sugars, water, organic acids, and other organic compounds, for example furfural and 5-hydroxymethylfurfural. The organic phase can be concentrated to remove volatile materials including the alcohol as well as residual water and some esters. However, it is difficult to remove all of the alcohol: the residue becomes increasingly viscous and difficult to handle as more alcohol is removed. In addition, if the residue following removal of alcohol is discarded, this results in an economic inefficiency from the loss of $C_{3-8}$ alkyl esters as well as other reaction products derived from the $C_{3-8}$ alkyl alcohol.

We have now found a process by which $C_{3-8}$ alkyl alcohol can be recovered from the organic phase much more efficiently than is possible by simple removal of alcohol.

SUMMARY OF THE INVENTION

The present invention provides a method of processing an aqueous hemicellulosic stream containing lignin, comprising:
(a) contacting an aqueous hemicellulosic stream containing lignin with a $C_{3-8}$ alkyl alcohol at elevated temperature and acidic pH;
(b) separating the reaction mixture obtained from step (a) into an aqueous phase containing hemicellulose-derived monosaccharide and an organic phase containing $C_{3-8}$ alkyl alcohol;
(c) concentrating the organic phase obtained from step (b) to remove at least some $C_{3-8}$ alkyl alcohol;
(d) treating the residue from step (c) with water or an aqueous medium having an alkaline pH; and
(e) recovering $C_{3-8}$ alkyl alcohol from the product of step (d).

DETAILED DESCRIPTION OF THE INVENTION

Recovery of $C_{3-8}$ Alkyl Alcohol, Steps (c) to (e)

The present invention provides an efficient way of treating a hemicellulose stream containing lignin with a $C_{3-8}$ alkyl alcohol, and recovering $C_{3-8}$ alkyl alcohol at the end of the process. Key to the process of the invention is the treatment of the residue obtained after removing at least some $C_{3-8}$ alkyl alcohol from the organic phase obtained in step (b) of the process.

In step (c), $C_{3-8}$ alkyl alcohol is removed from the organic phase obtained in step (b), thus producing a concentrated residue. Preferably, the concentration is carried out to a point such that the maximum amount of alcohol is removed without causing the residue to become a solid, an immobile liquid, or so viscous that further processing is not practical. The optimal extent of concentration will depend on the source and history of the feed stream for step (a). For example, in some embodiments, the concentration step (c) removes a proportion of the $C_{3-8}$ alkyl alcohol that was present in the organic phase in the range of from 50% to 90%, from 60% to 80%, or from 65% to 75% w/w. The removal may be carried out by any suitable method, for example by distillation, evaporation, and/or membrane-based concentration. Preferably the alcohol is removed by distillation or evaporation. Step (c) can be carried out in two or more stages, using the same or a different method. For example two or more distillation stages may be present, or a first stage may be distillation and a second stage evaporation.

The optimal temperature at which distillation is carried out will depend on the exact constitution of the organic phase obtained from step (b). Generally, distillation will be carried out at ambient pressure at a temperature in the range of from 90 to 140° C., for example 100 to 140° C., although lower temperatures may be used if the distillation is carried out under reduced pressure. Initially, the distillate is likely to be an alcohol/water azeotrope. Other volatile organic compounds may also be removed. The distillation may be carried out as a single step, or two or more separate distillation steps may be used.

Evaporation may be carried out using flash evaporation, vacuum evaporation, rotary evaporation or centrifugal evaporation. Types of evaporator that may be used include for example forced circulation evaporators, falling film evaporators, wiped film evaporators, rising film evaporators, falling-film plate evaporators and multiple effect evaporators. Evaporation may be carried out as a single step, or two or more separate evaporation steps may be used. When more than one evaporation step is used, different types of evaporator may be used for the different steps.

After $C_{3-8}$ alkyl alcohol is removed in step (c) of the process of the invention, the residue still contains some $C_{3-8}$ alkyl alcohol as well as $C_{3-8}$ alkyl esters and other reaction products derived from the $C_{3-8}$ alkyl alcohol. Typically, if the maximum amount of $C_{3-8}$ alkyl alcohol has been removed without causing the residue to become solid or otherwise intractable, the residue contains about 20 to about 60% w/w (or alternatively about 10 to about 30% w/w) of $C_{3-8}$ alkyl moieties based on the mass of the residue. Below this point, the residue tends to be a viscous, dark liquid, which is difficult to handle and which at lower temperatures can solidify, fouling equipment. In step (d) of the process of the invention, this residue is treated with an aqueous medium having a pH of 7 or more. This has the effect of releasing further $C_{3-8}$ alkyl alcohol, which can be recovered in step (e) of the process of the invention.

The water or aqueous medium used in step (d) must have a pH of 7 or more. Water at pH 7 may be used, but in one preferred embodiment of the invention, the aqueous medium is strongly alkaline. It may for example have a pH of at least 10, for example at least 12.

In one embodiment, the aqueous medium is an aqueous solution of an alkali metal hydroxide, for example potassium or, especially, sodium hydroxide.

In an alternative and particularly preferred embodiment, the highly alkaline medium is an alkaline stream which is obtained from the same industrial plant on which the feedstock hemicellulose stream is produced, as a product of the treatment of biomass. Particularly, the stream may be a product of a Kraft dissolving pulp process. In particular, the stream may be a white liquor stream. White liquor is an aqueous solution of sodium hydroxide and sodium sulfide, also generally containing additional compounds such as so-called "dead-load" sodium compounds, for example sodium carbonate, sodium thiosulfate, sodium sulfate and sodium sulfite, and has a very high pH, typically 14 or more.

In an alternative preferred embodiment, the highly alkaline medium is a black liquor stream. Black liquor streams have a very high pH, typically up to 12 or even higher. The residue from step (c) may be mixed with a black liquor stream from an alkaline pulping process, particularly Kraft pulping.

As an alternative to using a white or black liquor stream, and depending upon the local availability of highly alkaline streams, the highly alkaline stream may be green liquor (an aqueous stream produced by the incineration of black liquor, which contains sodium carbonate and sodium sulfide); or a mixture of any of black, white and green liquors.

Suitably, the residue from step (c) is maintained in liquid form. To this end, the residue is preferably maintained at elevated temperature, for example at a temperature of at least 60, especially at least 90, for example from 100 to 125° C. Step (d) is preferably carried out at elevated temperature, for example at a temperature of at least 100, especially at least 105, or at least 110° C., up to 130° C., for example from 110 to 130° C.

After treatment with the aqueous medium in step (d), further $C_{3-8}$ alkyl alcohol may be removed from the residue in step (e), for example by evaporation or distillation. The alcohol may for example be removed as an alcohol/water azeotrope. The optimal temperature at which distillation or evaporation may be carried out in step (e) will depend on the exact constitution of the mixture obtained from step (d). Generally, the distillation or evaporation will be carried out at a temperature in the range of from 90 to 120° C. The temperature range of from 90 to 120° C. is especially suitable for operation at atmospheric pressure. If the pressure is higher or lower, then a higher or lower temperature may be most appropriate. Primarily, the distillate is likely to be an alcohol/water azeotrope. For lower molecular weight alcohols, the distillate will initially be an alcohol/water azeotrope, followed thereafter by water. For lower molecular weight alcohols, the distillate will initially be an alcohol/water azeotrope, followed thereafter by alcohol. The conditions discussed above for step (c) may be applied.

Where an aqueous medium with an alkaline pH is used in step (d), $C_{3-8}$ alkyl esters as well as other reaction products derived from the $C_{3-8}$ alkyl alcohol which are present in the residue, may be hydrolysed to form additional $C_{3-8}$ alkyl alcohol, which is recovered in step (e) along with $C_{3-8}$ alkyl alcohol remaining in the residue.

In a preferred embodiment of the process of the invention, an optional additional step (f) is carried out in which $C_{3-8}$ alkyl alcohol recovered in step (c) and/or step (e) is recycled back to step (a) of the process.

After step (e) has been carried out, a further residue remains. This contains lignin and lignin-derived products, and if desired, such products may be recovered from this residue. A preferred way of doing this is described below. Alternatively, the further residue may be incinerated, for example in the recovery boiler of a dissolving pulp mill.

Overall, the process of the invention including carrying out steps (c) to (e) and optionally (f) provides an efficient and economical way of treating a hemicellulosic stream containing lignin, and can offer synergistic benefits from integration with existing biomass treatment operations, while maximising the efficient use of input chemicals.

The Aqueous Hemicellulosic Stream

As discussed above, hemicellulose is one of the three principal components of biomass, together with cellulose and lignin. Hemicelluloses are the second most abundant biopolymer in the plant kingdom after cellulose and they constitute, in general, 15-35% of plant biomass. Whereas cellulose is a highly uniform linear polysaccharide (it is a 1→4-β-linked polyglucan), the term hemicellulose defines a group of heterogeneous polysaccharides of comparatively low molecular weight, having a degree of polymerisation of from about 40 to about 600 (in many cases the degree of polymerisation is from about 80 to about 200). Most hemicelluloses are branched structures (see for example Ren and Sun, *Cereal Straw as a Resource for Sustainable Biomaterials and Biofuels; Chemistry, Extractives, Lignins, Hemicelluloses and Cellulose*, 2010, Chapter 4; also Girio et al, Bioresource Technology, 2010, 101 p 4775-4800).

Hemicelluloses have been classified into four groups: i) xyloglycans (xylans); ii) mannoglycans (mannans); iii) xyloglucans (XG); and iv) mixed-linkage β-glucans (Ren and Sun, *Cereal Straw as a Resource for Sustainable Biomaterials and Biofuels; Chemistry, Extractives, Lignins, Hemicelluloses and Cellulose*, 2010, Chapter 4).

Xylans comprise a β(1→4)-D-xylanopyranose backbone, and typically contain carbohydrate groups on the 2- or 3-position of backbone residues. Examples include glucuronoxylans (GX), arabino(glucurono)xylans (AGX), glucurono(arabino)xylans (GAX) and arabinoxylans (AX). Xylans are the most common hemicelluloses, and in particular are abundant in hardwood or annual plants.

Mannans have been categorised in two groups: i) galactomannans, which comprise a β(1→4) linked D-mannopyranose backbone; and ii) glucomannans, which have a backbone comprising D-mannopyranose and D-glucopyranose residues with β(1→4) linkages. Mannans may have varying degrees of branching, with D-galactopyranose groups on the 6-position of the mannose backbone.

Xyloglucans (XG) comprise a β(1→4)-linked D-glucopyranose backbone with D-xylanopyranose residues at the 6-position of glucopyranose residues. There are two categories of xyloglucans, depending on the nature of the xylanopyranose-containing side-chains. Xyloglucans comprising two xylanopyranose units followed by two glucanopyranose units are referred to as XXGG, and xyloglucans comprising three xylanopyranose units followed by one glucopyranose unit are referred to as XXXG. Additional side-chains may also be present.

Mixed linkage β-glucans have a D-glucopyranose backbone with mixed β linkages (1→3, 1→4).

Step (a) of the process of the invention involves contacting an aqueous hemicellulosic stream which also contains lignin with a $C_{3-8}$ alkyl alcohol at elevated temperature. In many industrial processes, following treatment of lignocellulosic biomass, a hemicellulosic stream and cellulosic solids are obtained and are separated from one another. The hemicellulosic stream contains a greater proportion by weight of hemicellulosic material relative to cellulosic material than the proportion by weight of hemicellulosic material relative to cellulosic material present in the lignocellulosic biomass itself. In other words, the hemicellulosic stream contains a fraction of lignocellulosic biomass-derived material that is enriched in hemicellulosic material over that present in the lignocellulosic biomass itself. Similarly, the cellulosic solids contain a greater proportion by weight of cellulosic material (i.e. cellulose and/or cellulose-derived saccharides) relative to hemicellulosic material than the proportion by weight of cellulosic material relative to hemicellulosic material present in the lignocellulosic biomass itself.

In one embodiment at least 60 wt %, or at least 70 wt %, or at least 80 wt %, or at least 90 wt %, or at least 95 wt % of the saccharide material present in the aqueous hemicellulosic stream is hemicellulosic material. In one embodiment less than 20 wt %, or less than 15 wt %, or less than 10 wt %, or less than 5 wt % of the saccharide material present in the aqueous hemicellulosic stream is cellulosic material. In one embodiment the aqueous hemicellulosic stream is free or substantially free of cellulosic material. In one embodiment at least 60 wt % of the lignocellulosic biomass-derived material present in the hemicellulosic stream is hemicellulosic material and less than 20 wt % of the lignocellulosic biomass-derived material present in the hemicellulosic stream is cellulosic material. In one embodiment at least 70 wt % of the lignocellulosic biomass-derived material present in the hemicellulosic stream is hemicellulosic material and less than 15 wt % of the lignocellulosic biomass-derived material present in the hemicellulosic stream is cellulosic material. In one embodiment at least 80 wt % of the lignocellulosic biomass-derived material present in the hemicellulosic stream is hemicellulosic material and less than 10 wt % of the lignocellulosic biomass-derived material present in the hemicellulosic stream is cellulosic material. The analysis of saccharide material may routinely be performed by liquid chromatographic methods, as described in standard procedures issued by organisations such as ASTM [D5896-96 (2012)], the National Renewable Energy Laboratory (TP-510-42623) and TAPPI (T-249).

The aqueous hemicellulosic stream also contains lignin, possibly together with lignin-derived products. The amount of lignin and lignin-derived products is highly variable and will depend upon the biomass processing used to produce the hemicellulosic stream. Such streams may be obtained by the processing of biomass by dissolving pulp processes such as those that may be operated at a Kraft pulp mill, or the sulfite process. For example, the hemicellulosic stream may have been obtained by using one of the processes described in more detail below. It may for example have been obtained by the hydrolysis of wood chips using hot water under pressure, or using steam. Preferably the hemicellulosic stream has been obtained from a dissolving pulp process; such streams are referred to as "pre-hydrolysis liquors", or PHL.

The concentration of hemicellulosic material present in the aqueous hemicellulosic stream will be a characteristic of the biomass source and will depend on the conditions used to obtain the aqueous hemicellulosic stream from biomass. In one embodiment at least 1 wt %, at least 5 wt %, at least 10 wt %, at least 20 wt %, at least 30 wt %, at least 40 wt % or at least 50 wt % of the aqueous hemicellulosic stream is hemicellulosic material.

The hemicellulosic material in the hemicellulosic stream comprises hemicellulose, hemicellulose-derived oligosaccharides and/or hemicellulose-derived monosaccharides. Hemicellulose-derived oligosaccharides and monosaccharides may be obtained by hydrolysis of hemicellulose present in biomass. The proportions of the hemicellulose, hemicellulose-derived oligosaccharides and/or hemicellulose-derived monosaccharides present in the hemicellulosic stream will depend on the conditions used to obtain the hemicellulosic stream from lignocellulosic biomass.

Constituents of hemicellulose typically have a significant degree of acylation, for example, xylan hemicellulose is often found in a highly acylated form. Conditions used for separating hemicellulosic material from cellulosic material typically result in significant quantities of organic acids, for example acetic acid or formic acid, being present in the hemicellulosic stream.

The aqueous hemicellulosic stream may be obtained from lignocellulosic biomass by known methods. For example, selective separation of hemicellulosic material from lignocellulosic biomass may be achieved using alkaline agents (such as sodium, potassium, calcium or ammonium hydroxide). The hemicellulosic stream may also be obtained by ammonia fibre explosion (AFEX). In that process, lignocellulosic biomass is treated with liquid ammonia at a temperature in the range of from 40 to 140° C. under pressure (250 to 300 psi), the complex formed by lignin with hemicellulose and cellulose is broken down and some hydrolysis of hemicellulose takes place. In another example, a hydrothermal process such as autohydrolysis (use of compressed liquid hot water, e.g. at a temperature in the range of from 200 to 250° C.) or steam injection/steam explosion (e.g. treatment with steam at a temperature in the range of from 200 to 250° C.) may be used. In a further example, biomass may be treated with an alcohol at high temperature, using the so-called "organosolv" process.

In one preferred embodiment, the aqueous hemicellulosic stream used in the process of the invention is obtained from a process for producing dissolving pulp. As discussed above, such processes typically involve an additional "pre-hydrolysis" stage in which lignocellulosic biomass is treated to remove hemicellulosic material and lignin/lignin-derived products, prior to subjecting the remainder of the cellulosic solids to further pulping conditions, such as Kraft conditions (treatment with an aqueous solution of sodium hydroxide and sodium sulphide at elevated temperature) or sulfite conditions (treatment with aqueous metal sulfite and/or bisulfite at elevated temperature). Preferred pre-hydrolysis conditions comprise contacting lignocellulosic biomass such as wood chips with water at elevated temperature, optionally in the presence of an acid catalyst. For example, in one particularly preferred embodiment lignocellulosic biomass is treated with dilute sulfuric acid (e.g. 0.2-5% v/v aqueous sulfuric acid, or at a sulfuric acid concentration in water of from 0.05M to 1.5M) at a temperature in the range of from 100 to 250° C., more preferably in the range of from 150 to 250° C. In another embodiment lignocellulosic biomass is treated with concentrated sulfuric acid (e.g. 10-30% v/v aqueous sulfuric acid, or at a sulfuric acid concentration in water of from 2.0M to 6.0M) at a temperature in the range of from 40 to 100° C.

Pre-hydrolysis liquor typically contains high quantities of hemicellulosic material as well as lignin and is particularly suitable for use in the process of the invention.

In one embodiment, the aqueous hemicellulosic stream used in the process of the invention is a hemicellulose-containing black liquor. As discussed above, black liquor is a by-product of the Kraft process and is an aqueous mixture which may contain hemicellulosic material together with lignin/lignin-derived products and inorganic chemicals (e.g. sodium sulphate, sodium carbonate). Typically, the black liquor obtained following digestion of biomass (e.g. wood chips) contains approximately 15% by weight solid material, and is termed weak black liquor. Subsequent processing of the weak black liquor, for example by evaporating water, results in a substance which typically contains up to about 65 to 80% by weight solid material, which is termed heavy black liquor.

In one embodiment, the aqueous hemicellulosic stream used in the process of the invention is brown liquor. As discussed above, brown liquor is a by-product of the sulfite process for making wood pulp, and is an aqueous mixture containing hemicellulosic material, lignin/lignin-derived products and inorganic chemicals. Brown liquor is also referred to as red liquor, thick liquor, spent liquor and sulfite liquor.

In one embodiment, the aqueous hemicellulosic stream used in the process of the invention is a hemicellulosic waste stream from a process for producing bioethanol (e.g. a process for producing bioethanol involving fermentation of cellulose hydrolysate).

In one embodiment, the aqueous hemicellulosic stream is a hemicellulosic stream from a process for producing sugars from biomass.

In one embodiment, the aqueous hemicellulosic stream is a hemicellulosic stream obtained by the "organosolv" process which involves the treatment of biomass with an alcohol.

In one embodiment, the aqueous hemicellulosic stream is obtained by the treatment of cellulosic material for disposal purposes.

The hemicellulosic stream may result from the treatment of any suitable lignocellulosic biomass. For example, the biomass may be wood chips; food waste products; or non-food waste products, for example corn-derived non-food wastes such as corn stover or corn pericarp, or sugar cane bagasse.

The proportions of hemicellulose, cellulose and lignin present in lignocellulosic biomass vary depending on the type of biomass, as do the proportions of different polysaccharides which make up the hemicellulose proportion of the biomass. In one preferred embodiment the biomass from which the hemicellulosic stream is obtained comprises a hardwood, for example an *Acer* (maple), *Populus* (aspen), *Betula* (birch), *Fagus* (beech), *Eucalyptus, Quercus* (oak) *Populus* (poplar) or *Liquidambar* (sweetgum). In one preferred embodiment the biomass from which the hemicellulosic stream is obtained comprises a softwood, for example an *Abies* (fir), *Larix* (larch), *Picea* (spruce) or *Pinus* (pine). In one preferred embodiment the biomass from which the hemicellulosic stream is obtained comprises a grass, for example a *Panicum* (e.g. *Panicum virgatum*, switch grass), a *Sorghum* (e.g. sweet sorghum) or a *Saccharum* (e.g. sugar cane).

If desired, the hemicellulosic stream may be pre-treated before carrying out step (a). In one embodiment no pre-treatment is carried out. In another embodiment, the hemicellulosic stream is concentrated to increase its solids content.

Step (a)

In one preferred embodiment the $C_{3-8}$ alkyl alcohol used in step (a) of the process of the invention contains only one hydroxyl group. Examples of preferred alkyl alcohols include i-propanol, n-butanol, n-pentanol, n-hexanol and 2-ethylhexanol.

In one preferred embodiment, the alkyl alcohol is a $C_{4-8}$ alkyl alcohol containing only one hydroxy group. Most preferably the $C_{3-8}$ alkyl alcohol is n-butanol, and throughout this Specification, except where the context requires otherwise, any reference to a $C_{3-8}$ alkyl alcohol should be taken to include a specific reference to n-butanol.

Step (a) is carried out at acidic pH, i.e. at a pH of less than 7. Preferably step (a) is carried out at a pH of less than 5, less than 4, less than 3 or less than 2. If the aqueous hemicellulosic stream is itself acidic, simply contacting the hemicellulosic stream with $C_{3-8}$ alkyl alcohol at elevated temperature may be sufficient to hydrolyse hemicellulose to sugars and/or to produce $C_{3-8}$ alkyl esters from any acids, for example acetic acid, present in the hemicellulosic stream. However, in some cases it may be preferred to add an acid in step (a). Where an acid is added in step (a), it may for example be a mineral acid, or an organic acid such as trifluoroacetic acid or methanesulfonic acid. Alternatively a solid-state resin can be added as an acid catalyst. Preferably the acid added in step (a) is a mineral acid, more preferably a mineral acid selected from the group consisting of hydrochloric acid and sulfuric acid (e.g. concentrated hydrochloric acid or concentrated sulfuric acid). In one embodiment the acid is hydrochloric acid. In another embodiment the acid is sulfuric acid. In one embodiment concentrated sulfuric acid or concentrated hydrochloric acid is added, in a volume ratio in the range of from 0.1:100 to 3:100 relative to the total volume of solvent used in step (a).

Preferably step (a) is carried out at a temperature in the range of from 30 to 250° C.; more preferably in the range of from 70 to 200° C.; still more preferably in the range of from 130 to 190° C., for example from 130 to 170° C., or from 140 to 180° C. Where the $C_{3-8}$ alkyl alcohol used in step (a) is n-butanol, step (a) is for example carried out at a temperature in the range of from 130 to 170° C. or from 140 to 180° C. The use of higher temperatures can reduce the reaction time leading to improved process economics; alternatively, the use of lower temperatures can result in acceptably high yields of monosaccharides although longer reaction times or higher catalyst loadings, or both, may be necessary.

Step (a) may be carried out as a batch operation, or may be performed in a continuous manner. For example, step (a) may be carried out in continuous fashion, for example using one or more, for example two or more, continuous reactors, for example stirred tank reactors, in series.

At the high end of the above temperature range, the reaction may be complete in as little as a few minutes. At lower temperatures, the time taken may be much longer. Where step (a) is carried out batchwise, it may for example be carried out over a time period of at least 5 minutes or for at least 10 minutes, up to for example 48 hours, or 24 hours, or 12 hours, or 6 hours.

In one preferred embodiment step (a) is carried out at a temperature in the range of from 70 to 200° C., for at least 5 minutes, over a time period of up to 12 hours, for example up to 6 hours; or a temperature in the range of 140 to 180° C. for a time period of from 5 minutes to 2 hours, especially 10 minutes to 1 hour; or at a temperature in the range of from 120 to 150° C. for a time period of from 5 minutes to 6 hours.

As discussed above, a hemicellulosic stream is a stream comprising hemicellulose, hemicellulose-derived oligosaccharides and/or hemicellulose-derived monosaccharides, and the proportions of those constituents will vary depending on the process by which the hemicellulosic stream has been obtained. Where the hemicellulosic stream contains hemicellulose and/or hemicellulose-derived oligosaccharides, subjecting the hemicellulosic stream to the conditions of step (a) results in hydrolysis of the hemicellulose and/or hemicellulose-derived oligosaccharides, such that the proportion of hemicellulosic material in the product of step (a) that is hemicellulose-derived monosaccharide is greater than the proportion of hemicellulosic material in the hemicellulosic stream starting material that is hemicellulose-derived monosaccharide. In one preferred embodiment, the hemicellulosic stream is subjected to the conditions of step (a) until at least 80 wt %, at least 90 wt %, at least 95 wt %, or all or substantially all of the hemicellulose-derived saccharides present in the reaction mixture are hemicellulose-derived monosaccharides. In an alternative embodiment, the hemicellulosic stream is subjected to the conditions of step (a) until just a small proportion (for example less than 10 wt %) of the hemicellulose-derived saccharides present in the reaction mixture are hemicellulose-derived monosaccharides. This alternative embodiment is especially desirable when it is required that a greater proportion of the sugars is in a non-hydrolysed state prior to the onward conversion. This may, for example, be the case when the onward conversion is to furfural.

Where an acid is added in step (a), the hemicellulosic stream may be admixed with acid prior to, at the same time as, or after admixing with $C_{3-8}$ alkyl alcohol. For example, $C_{3-8}$ alkyl alcohol may be added to the hemicellulosic stream followed by the acid, and the mixture then heated at elevated temperature. Alternatively, $C_{3-8}$ alkyl alcohol may be added to the hemicellulosic stream and heated to elevated temperature, followed by addition of the acid. Alternatively, the hemicellulosic stream may be first heated, then the $C_{3-8}$ alkyl alcohol and acid may be added. Alternatively, acid may be added to the hemicellulosic stream followed by the $C_{3-8}$ alkyl alcohol, and the mixture then heated at elevated temperature. Alternatively the acid may be added to the hemicellulosic stream and the mixture heated at elevated temperature, with the $C_{3-8}$ alkyl alcohol then being added and the resulting mixture being heated at elevated temperature for a further period. Alternatively the acid may be added to the $C_{3-8}$ alkyl alcohol, and the resulting mixture then added to the hemicellulosic stream and the mixture heated at elevated temperature.

Step (a) is typically carried out at ambient or autogenous pressure, but it may be carried out at higher or lower pressure if desired.

As discussed above, constituents of hemicellulose typically have a significant degree of acylation, and as hemicellulosic material is broken down in step (a) of the process of the invention, significant quantities of organic acids (e.g. acetic acid, formic acid) may be formed. Under the process conditions of step (a), a significant proportion of the organic acids and/or acyl moieties forming part of the hemicellulosic material in the hemicellulosic stream are converted to the corresponding $C_{3-8}$ alkyl ester, permitting separation of the alkyl ester and hemicellulose-derived saccharide in organic and aqueous phases respectively.

The conditions under which step (a) is carried out will determine whether the reaction mixture is a one-phase or a two-phase system. Generally, it may be preferred to carry out the reaction at a sufficiently high temperature for the reaction mixture to be a one-phase system. Cooling of a one-phase reaction mixture from step (a) will lead to a separation of the aqueous and organic phases, for separation in step (b).

Step (b)

In step (b), the products obtained from step (a) are separated into an aqueous phase and an organic phase. The hemicellulose-derived monosaccharides preferentially partition into the aqueous phase and lignin and lignin-derived products, together with $C_{3-8}$ alkyl esters and certain other organic products, preferentially partition into the organic phase.

As discussed above, where a $C_{4-8}$ alkyl alcohol containing only one hydroxy group is used, a biphasic mixture results following step (a) without the need for additional organic solvent. However, if desired, additional organic solvent and/or water may be added prior to separation. For example, additional organic solvent may be used to wash the aqueous phase following initial separation from the organic phase in order to improve the purity of the saccharides present in the aqueous phase. Similarly, additional water may be used for re-extraction of the separated organic phase before step (c) is carried out, to increase the quantity of saccharides obtained. In one preferred embodiment, where additional organic solvent is used in step (b) the additional organic solvent is a $C_{4-8}$ alkyl alcohol containing only one hydroxy group, and the same type of alkyl alcohol is used in steps (a) and (b); more preferably the $C_{4-8}$ alkyl alcohol used in step (a) and additional organic solvent used in step (b) are both n-butanol. If additional organic solvent or additional water is used, certain of the later process parameters (for example temperatures and times) may need to be altered to take account of the additional solvent and/or water that is present.

In step (b) the organic and aqueous phases may be separated by routine techniques; for example by removing the bottom layer from a vessel through a bottom run-off valve, by decanting or siphoning off the top layer, or in a liquid-liquid phase separator. Step (b) may be carried out at ambient temperature, or at a higher or lower temperature if desired. In a preferred embodiment, step (b) is carried out at elevated temperature, preferably at a temperature in the range of from 30 to 95° C., more preferably in the range of from 40 to 90° C. Step (b) is typically carried out at ambient pressure, but it may be carried out at higher or lower pressure if desired.

Step (b) may be carried out as a batch operation, or may be performed in a continuous manner. In a preferred embodiment, step (b) is carried out in a continuous manner. In a particularly preferred embodiment, step (a) and step (b) are carried out in a continuous manner with the flow of product from step (a) continuously filling a phase separator unit, the contents of which are continuously being separated.

Optional Additional Steps

The aqueous phase obtained from step (b) contains useful products, specifically, hemicellulose-derived monosaccharides, and these may be recovered, or may be converted into further useful products. Thus for example in an optional step (g), the hemicellulose-derived monosaccharide obtained within said aqueous phase is reacted with a metal hydroxide or quaternary ammonium hydroxide to produce metal lactate or quaternary ammonium lactate. The metal hydroxide may for example be lithium hydroxide, potassium hydroxide, calcium hydroxide, barium hydroxide, or, especially, sodium hydroxide. The quaternary ammonium hydroxides may for example be a tetraalkylammonium hydroxide such as tetramethylammonium hydroxide or tetraethylammonium hydroxide, or a benzylalkylammonium hydroxide such as benzyltrimethylammonium hydroxide. Full details of such reactions are given in WO 2015/155534. In one preferred embodiment of step (g), hemicellulose-derived monosaccharide is reacted with sodium hydroxide at a temperature in the range of from 50 to 140° C., typically over a time period in the range of from 15 minutes to 3 hours.

The metal lactate or quaternary ammonium lactate produced by the process of the invention when step (g) is included may for example be converted into lactic acid. Accordingly the process of the invention may also include an optional step (h) which comprises reacting at least a portion of the metal lactate or quaternary ammonium lactate produced in step (g) with an acid to produce lactic acid. Full details of such reactions are given in WO 2015/155534. Typically step (h) is carried out at ambient temperature, although higher or lower temperatures may be used if desired. The acid used in step (h) is preferably a mineral acid, for example hydrochloric acid or sulfuric acid.

Lactic acid produced in step (h) may also be converted into other downstream products such as, for example, an alkyl lactate, oligomeric lactic acid, lactide, alkyl lactyllactate, polylactic acid, or a complex of lactic acid and either ammonia or an amine. Thus the invention also provides a process for the preparation of one or more of these products comprising producing metal lactate or quaternary ammonium lactate by a process according to the invention, and converting the metal lactate or quaternary ammonium lactate into lactic acid, alkyl lactate, oligomeric lactic acid, lactide, alkyl lactyllactate, polylactic acid, or said complex.

When the hemicellulose stream is obtained from a hardwood source, the monosaccharide stream produced in aqueous solution in step (b) is expected to contain xylose. In such cases, the aqueous stream obtained from step (b) may be used to produce derivatives of xylose. Purification of the xylose may optionally be carried out first. The xylose present in the hemicellulose-derived monosaccharides may for example be used as a sugar source for fermentation processes to produce, for example, ethanol, n-butanol, i-butanol, lactic acid, xylitol, xylonic acid, itaconic acid, glutamic acid or proline.

Alternatively, the xylose present in the hemicellulose-derived monosaccharides may be used as a feed for chemical processes to produce, for example, xylitol, polyols (e.g. ethylene glycol, propylene glycol) and/or furfural.

When the hemicellulose stream is obtained from a softwood source, the monosaccharide stream produced in aqueous solution in step (b) is expected to contain hexose sugars including mannose, galactose and glucose. In such cases, the mixture of hexoses may be used to produce derivatives of mannose, galactose and glucose. Purification of the hexoses may optionally be carried out first. The galactose, mannose and/or glucose present in the hemicellulose-derived monosaccharides may be used as a sugar source for fermentation processes to produce, for example, ethanol, n-butanol, i-butanol, lactic acid, succinic acid, or acrylic acid. Alternatively the galactose, mannose and/or glucose present in the hemicellulose-derived monosaccharides may be used as a feed for chemical processes to produce, for example, sugar alcohols (e.g. sorbitol), polyols (e.g. ethylene glycol, propylene glycol), and/or 5-hydroxymethylfurfural.

Thus, the process of the invention may include an additional optional step (i) in which the hemicellulose-derived monosaccharide includes xylose, and the xylose is converted into ethanol, n-butanol, i-butanol, lactic acid, xylitol, xylonic acid, itaconic acid, glutamic acid, proline, ethylene glycol, propylene glycol, and/or furfural; and/or an additional optional step (j) in which the hemicellulose-derived monosaccharide includes mannose, galactose or glucose, and said mannose, galactose or glucose is converted into ethanol, n-butanol, i-butanol, lactic acid, succinic acid, sugar alcohols (e.g. sorbitol), polyols (e.g. ethylene glycol, propylene glycol), and/or 5-hydroxymethylfurfural.

The invention also provides a process for the preparation of ethanol, n-butanol, i-butanol, lactic acid, xylitol, xylonic acid, itaconic acid, glutamic acid, proline, ethylene glycol, propylene glycol, furfural, succinic acid, sorbitol, or 5-hydroxymethylfurfural, which comprises carrying out a process including steps (a) to (e) and converting the hemicellulose-derived monosaccharide obtained with said aqueous phase of step (b) into ethanol, n-butanol, i-butanol, lactic acid, xylitol, xylonic acid, itaconic acid, glutamic acid, proline, polyols (e.g. ethylene glycol, propylene glycol), propylene glycol, furfural, succinic acid, sugar alcohols (e.g. sorbitol), or 5-hydroxymethylfurfural.

Optional Recovery of Lignin

As mentioned above, it is possible to obtain lignin and lignin-derived products from the residue remaining after step (e) of the process has been carried out. In a particularly preferred embodiment, the concentrated organic material obtained from step (c) is treated with an alkaline solution (e.g. of sodium hydroxide) in step (d) to give an aqueous, alkaline solution containing lignin and lignin derived products, and other water soluble species (e.g. the degradation products obtained from treating residual saccharides with alkali). Treatment with an acid of the residue remaining after step (e) has been carried out when using this variant of step (d) results in the near quantitative precipitation of the lignin. This precipitation is highly selective, with organic and inorganic constituents of the residue other than lignin largely remaining in solution. In contrast, the use of water only in step (d) can result in lignin precipitation and lower butane recovery during step (e), and addition of acid after step (e) has no beneficial effect. Use of an alkaline solution in step (d) and acid treatment after step (e) is thus valuable if it is desired to recover lignin. Accordingly, in a preferred embodiment of the process of the invention, step (d) comprises treating the residue from step (c) with an aqueous medium having an alkaline pH, and the process includes an additional step (k) which comprises treating at least part of the residue remaining after step (e) has been carried out, with an acid, in order to precipitate lignin. Any suitable acid may be used, especially a mineral acid, for example hydrochloric or, especially, sulfuric acid. Most preferably concentrated sulfuric acid is used. The lignin is precipitated as a solid which may be recovered after optional washing and drying by methods such as e.g. filtration or decantation. Solid lignin may have a number of advantages. For example, it may be transported more readily if it is to be used as a fuel at a remote site, or for example, for fueling the lime kiln at a dissolving wood pulp mill.

General

Additional routine processing steps may be carried out at any stage of the process, e.g. to add or remove solvent. By way of example, the aqueous hemicellulosic stream may be concentrated to remove some water prior to carrying out step (a), and/or the aqueous phase obtained in step (b) may be concentrated to remove some water prior to carrying out step (g) (e.g. by distillation, evaporation or membrane separation).

The process of the invention may be carried out batch wise, or as a continuous or semi-continuous process. For example, the hemicellulosic stream may be processed as a succession of batches. Similarly, if desired, the hemicellulosic stream may be provided as a succession of batches (e.g. in a series of containers shipped from the location where the hemicellulosic stream is obtained from lignocellulosic biomass to the location where the process of the invention is carried out).

Figure 1:
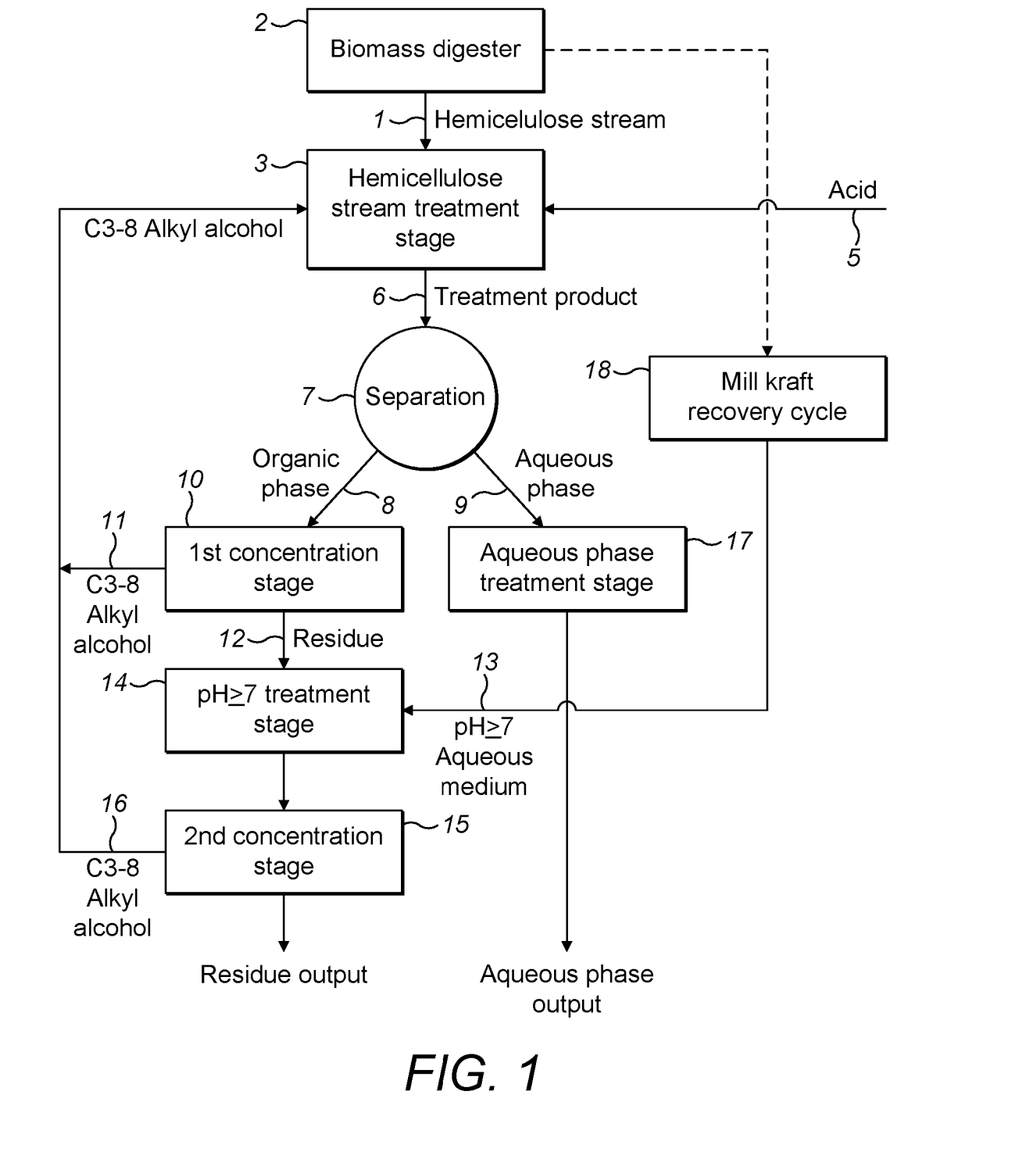
FIG. 1 is a flow diagram illustrating preferred embodiments of the invention.

FIG. 1 is a flow diagram illustrating preferred embodiments of the invention. In FIG. 1, an aqueous hemicellulose stream (1) obtained from a biomass digester (2) is passed to a treatment stage (3) where it is contacted with a $C_{3-8}$ alkyl alcohol (4), typically n-butanol, in the presence of an acid (5), typically sulfuric acid. The product (6) of that treatment stage is separated (7) into an organic phase (8) and an aqueous phase (9). The organic phase (8) is passed to a first concentration stage (10) where volatile products including $C_{3-8}$ alkyl alcohol (11) are removed. The residue (12) of the first concentration stage (10) is treated with an aqueous medium (13) having a pH of 7 or more, in treatment stage (14), and the resulting mixture is concentrated via a second concentration stage (15) to recover further $C_{3-8}$ alkyl alcohol (16).

Aqueous phase (9) is taken for further treatment (17) which may involve purification of hemicellulose-derived sugars, and/or conversion of hemicellulose-derived sugars into further products, for example lactic acid derivatives.

In optional but preferred embodiments, $C_{3-8}$ alkyl alcohol (11) and/or (16) are recycled to treatment stage (3). Aqueous medium (13) may be a further product stream obtained from a wood-pulping process, e.g. via recovery of streams from a Kraft process (18). The residue output from second concentration stage (15) may be treated with an acid, for example sulfuric acid, to precipitate lignin, which may be recovered. Alternatively said residue output may be passed to a recovery boiler for incineration.

The following Examples illustrate the invention.

Example 1

Production of Butanol Solution of Lignin (Steps a and b)

500 litres of PHL supplied from a Kraft dissolving pulp mill was evaporated from about 3.5% to 14.0% w/w hemicellulose sugars (i.e. the mass of monosaccharide obtained on hydrolysing the hemicellulose components, as per the method outlined in the National Renewable Energy Laboratory's Technical Report TP-510-4623, January 2008, *Determination of Sugars, Byproducts and Degradation Products in Liquid Fraction Process Samples*).

A mixture comprising 12,000 g of the concentrated PHL (14.0% w/w hemicellulose sugars), 5000 g of n-butanol and 192 g concentrated sulfuric acid was then prepared and filtered to remove a small amount of fine precipitate. 1350 ml of the mixture was then pumped into a 2 litre pressure reactor equipped with stirrer and a condenser and heated to 150° C. (as measured by an internal thermocouple). Once the internal temperature had reached steady conditions, a second pump controlling output flow was started, and the two pumps were quickly balanced to ensure a constant volume of reactants within the vessel.

The experiment was run with a steady input flow rate of 3600 g/hr for about 5 hours. The mean residence time with the reactor was calculated to be 22.8 minutes. HPLC (ion chromatography) indicated typical conversions of the hemicellulose to monosaccharide sugars of 60-62%.

The products from this stage were then re-fed through the reactor under identical conditions (in order to replicate a two stage CSTR process). As before the temperature was maintained at 150° C. and a mean residence time of 22.8 minutes was used. HPLC (ion chromatography) indicated typical conversions of the original hemicellulose content to monosaccharide sugars of 68-72%.

The output from the second CSTR model stage was then transferred to a jacketed 20 litre glass reactor equipped with a bottom drain valve. After cooling to about 90° C., biphasic separation was noted to occur quickly. Phase separation was then performed at 60° C. by draining the denser aqueous layer from the bottom of the vessel. The remaining n-butanol solution of lignin and other components including n-butyl esters was finally transferred to a plastic drum and used as a feedstock for the following Examples.

Example 2 (Comparative)

Recovery of Alkyl Alcohol without Step (d) (i.e. without Addition of Water or Aqueous Alkaline Solution)

1690 g of an n-butanol solution containing lignin arising from Example 1 was charged to a 2 litre jacketed glass reactor fitted with an overhead stirrer and a side-arm distillation assembly, and heated with oil supplied from a circulating bath. The mixture was stirred at 300 rpm and heated to boiling point (92.4° C.) at ambient pressure. A biphasic distillate was removed continuously until the temperature of the mixture reached 115° C. At this point 1043 g of the biphasic distillate was removed.

A sample of the partially concentrated n-butanol solution containing lignin was tested for n-butanol content by gas chromatography (GC) and found to be 47% w/w [i.e. 304 g n-butanol (47% of 647 g):343 g lignin and other components, e.g. n-butyl esters].

The remaining mixture was stirred at 300 rpm and heated to boiling point (61.6° C.) at a reduced pressure of 125 mbar. The monophasic distillate was removed continuously until the temperature of the mixture reached 90° C. and the viscosity of the mixture visibly increased. A total of 223.5 g of distillate was removed.

The mixture was discharged from the reactor via a heat-traced bottom drain valve and cooled to ambient temperature, yielding a black semi-pliable solid. This was analysed for n-butanol content by headspace gas chromatography (Headspace-GC) and found to be 12.5% w/w (retention time 4.6 min). The GC trace is shown in FIG. 2.

Figure 2:
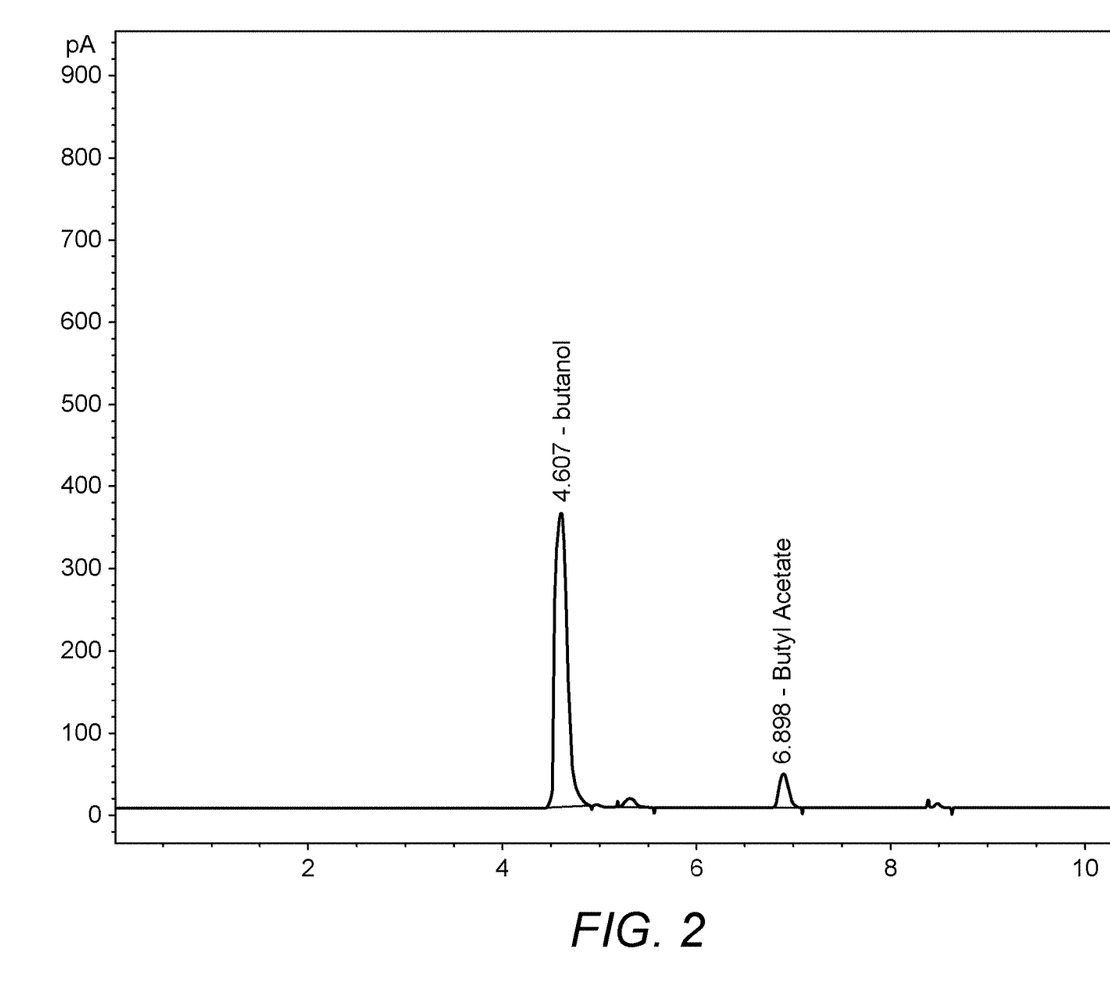
FIG. 2 shows the results of Example 2.

The chromatogram in FIG. 2 clearly shows the presence of n-butyl acetate (retention time=6.9 min). Further analysis indicates that the concentration of the n-butyl acetate was 4-5% w/w.

Example 3

Recovery of Alkyl Alcohol with Step (d) Using Water 1447 g of an n-butanol solution containing lignin arising from Example 1 was charged to a 2 litre pear-shaped flask and using a rotary evaporator, biphasic distillate was removed at a temperature of 60° C. and decreasing pressure of 140 to 50 mbar until 385.6 g concentrated n-butanol solution containing lignin remained.

A sample of the partially concentrated n-butanol solution containing lignin was tested for n-butanol content by gas chromatography (GC) and found to be 31% w/w (i.e. 119.5 g n-butanol:266.1 g lignin and other components, e.g. n-butyl esters).

112.8 g of this concentrated n-butanol solution of the lignin-hemicellulose mixture and 81.5 g demineralised water were then charged to a 200 ml oil-heated jacketed glass reactor fitted with an overhead stirrer and a side-arm distillation assembly. The mixture was stirred at 300 rpm and heated to boiling point (95° C.) at ambient pressure. Biphasic distillate was removed continuously and fresh water was added back into the reactor at an equivalent rate to the distillate take-off until the temperature of the mixture reached 100° C. and 70 ml of biphasic distillate had been removed.

The mixture was discharged from the reactor via the bottom drain valve, yielding a dark-brown liquor and a black, gum-like solid. The liquor (135 g) was decanted off and the wet solid (50 g) was dried overnight in an oven at 60° C. producing 38 g of dry solid. A sample of the dry solid was tested for n-butanol content by Headspace-GC and found to be 5.1% w/w. The GC trace is shown in FIG. 3.

Figure 3:
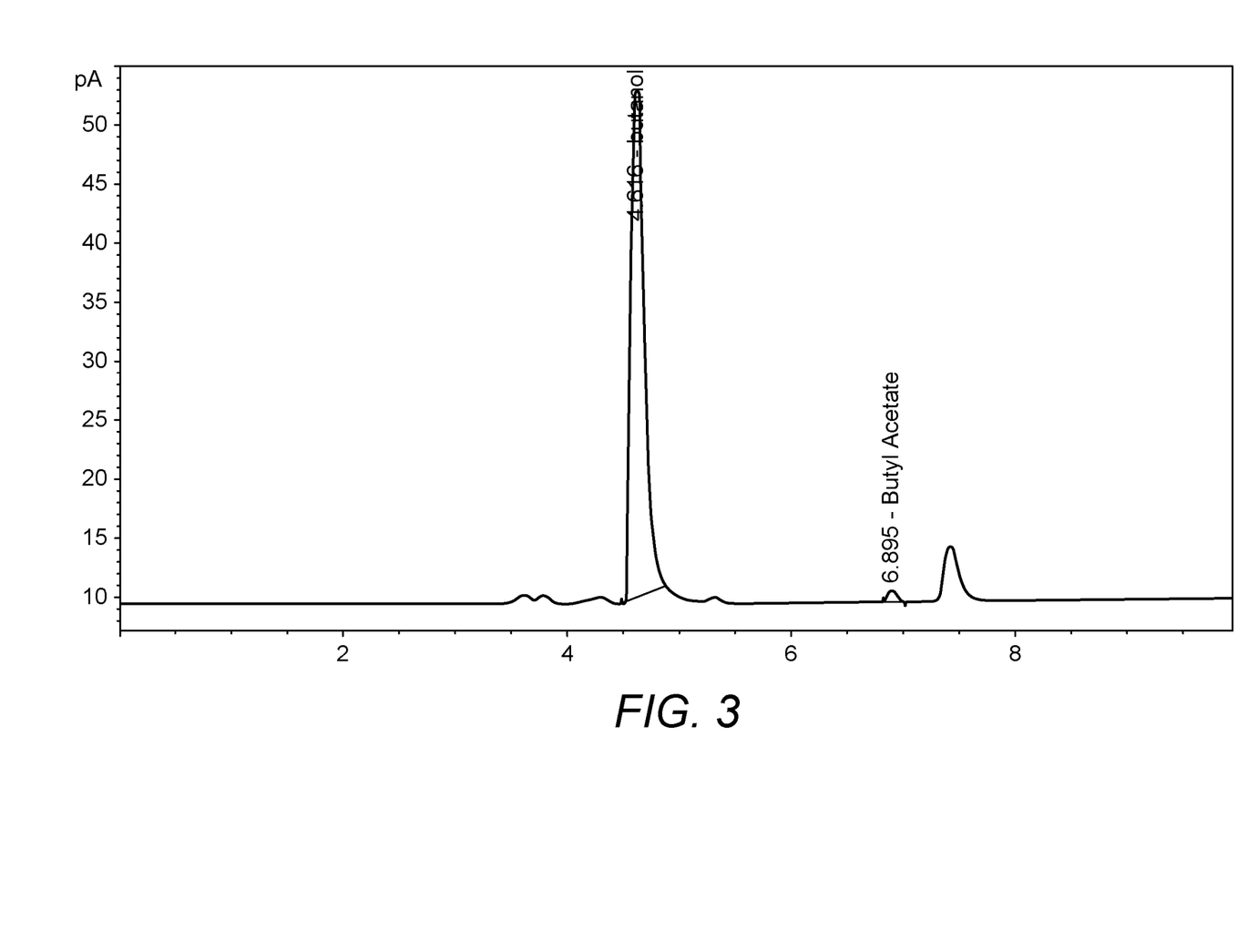
FIG. 3 shows the results of Example 3.

The chromatogram in FIG. 3 clearly shows the presence of n-butyl acetate (retention time=6.9 min). Further analysis indicates that the concentration of the n-butyl acetate was 4-5% w/w.

Example 4

Recovery of Alkyl Alcohol with Step (d) Using Sodium Hydroxide Solution 101.8 g of the concentrated n-butanol solution produced in Example 3 (i.e. 31% w/w n-butanol) was charged to a 200 ml oil-heated jacketed glass reactor fitted with an overhead stirrer and a side-arm distillation assembly. The mixture was stirred at 300 rpm and 70.8 g of 3.2M sodium hydroxide solution was added dropwise from a dropping funnel and this mixture was then heated to boiling point (96° C.) at ambient pressure. Biphasic distillate was removed continuously and fresh water was added back into the reactor at an equivalent rate to the distillate take-off until the temperature of the mixture reached 103° C. and 72 ml of biphasic distillate had been removed.

The mixture was discharged from the reactor via the bottom drain valve, yielding 182.3 g of a black coloured liquor and no visible solids. The liquor was tested for n-butanol content by Headspace-GC and found to be 0.5% w/w (equivalent to 2.6% w/w based on the dry lignin solids components). The GC trace is shown in FIG. 4.

Figure 4:
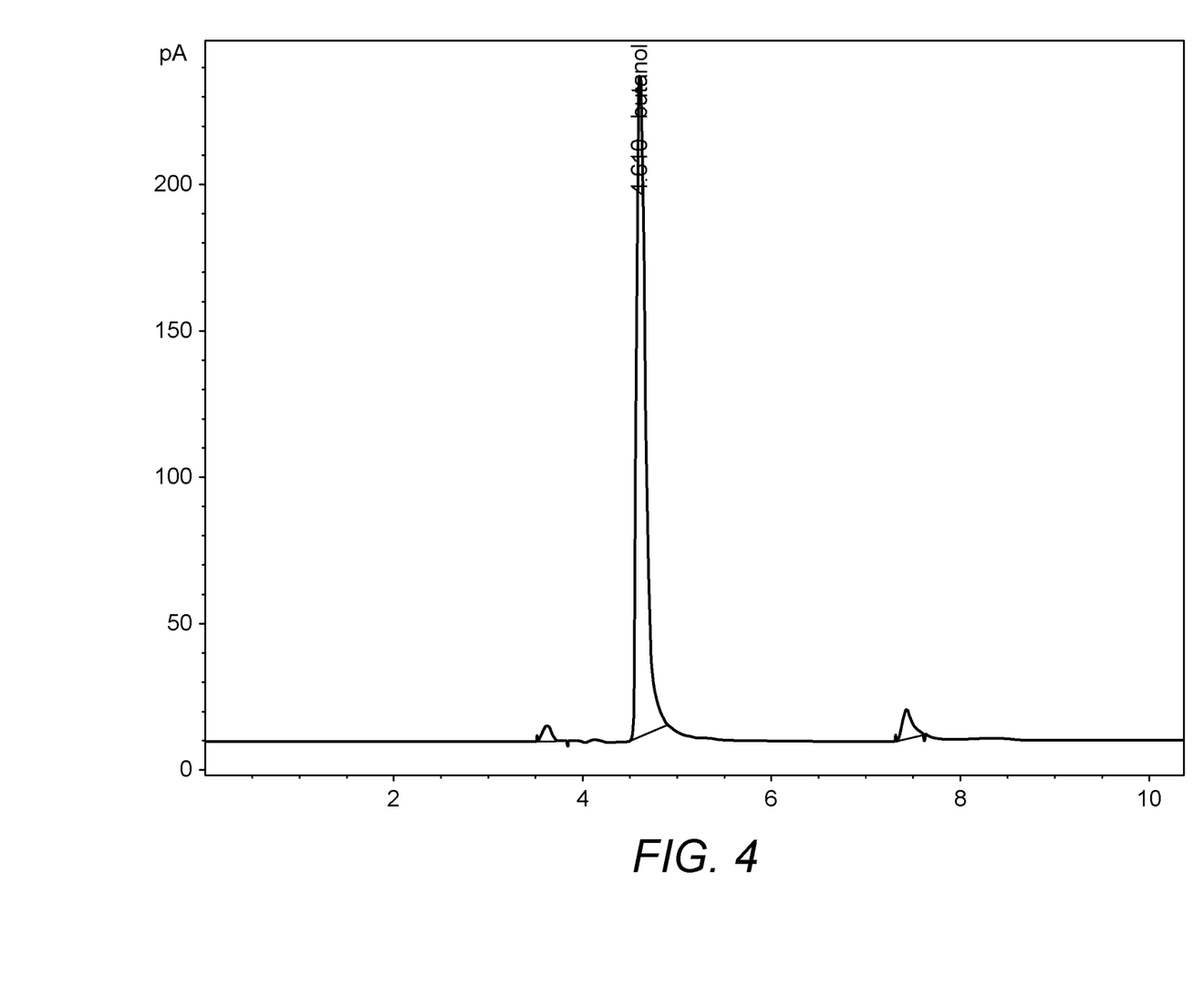
FIG. 4 shows the results of Example 4.

The chromatogram shown in FIG. 4 is notably different from FIGS. 2 and 3 as no signal is observed for n-butyl acetate. This demonstrates that the use of aqueous alkaline solutions in step (d) results in a higher recovery efficiency of n-butanol due to the hydrolysis of n-butyl acetate and other n-butyl esters.

Example 5

Production of Butanol Solution of Lignin 100 litres of a PHL supplied from a Kraft dissolving wood pulp mill was evaporated to 14.4% w/w hemicellulose sugars (i.e. the mass of monosaccharide obtained on hydrolysing the hemicellulose components, as per the method outlined in the National Renewable Energy Laboratory's Technical Report TP-510-4623, January 2008, Determination of Sugars, Byproducts and Degradation Products in Liquid Fraction Process Samples).

15443 g of the concentrated PHL (14.4% w/w hemicellulose sugars), 6361 g of a simulated n-butanol re-cycle stream (comprising of 72% w/w n-butanol, 21% w/w water, 4% w/w n-butyl acetate, and a number of other organic species) and 60.7 g concentrated sulfuric acid were mixed together. 1350 ml of the mixture was then pumped into a 2 litre pressure reactor equipped with stirrer and a condenser and heated to 150° C. (as measured by an internal thermocouple). Once the internal temperature had reached steady conditions, a second pump controlling output flow was started, and the two pumps were quickly balanced to ensure a constant volume of reactants within the vessel. The experiment was run with a steady input flow rate of 3700 g/hr for about 6 hours. The mean residence time with the reactor was calculated to be 24 minutes.

The product liquor from this stage was then re-fed through the reactor (in order to replicate a two stage CSTR process) at 150□. Chromatographic analysis of the aqueous components of aliquots removed throughout the reaction indicated typical conversions of the original hemicellulose content to monosaccharide sugars of 64-70%.

The output from the second CSTR model stage was then transferred to a jacketed 20 litre glass reactor equipped with a bottom drain valve. Phase separation was performed at 60° C. by draining the denser aqueous layer from the bottom of the vessel. The remaining n-butanol solution of lignin and other components including n-butyl esters was finally transferred to a plastic drum and used as a feedstock for the following Examples.

Example 6

Recovery of Alkyl Alcohol without Addition of Aqueous Alkaline Solution 5841.5 g of an n-butanol solution containing lignin arising from Example 5 was charged to a 5 litre jacketed glass reactor fitted with an overhead stirrer and a side-arm distillation assembly, and heated with oil supplied from a circulating bath. The mixture was stirred at 300 rpm and heated to boiling point (92.4° C.) at ambient pressure. A biphasic distillate was removed continuously until the temperature of the mixture reached 115° C. At this point 3725 g of the biphasic distillate was removed.

A sample of the partially concentrated n-butanol solution containing lignin was tested for n-butanol content by gas chromatography (GC) and found to contain 49% w/w [i.e. 1037 g n-butanol (49% of 2116 g):1079 g lignin and other components, e.g. n-butyl esters].

Example 7

Recovery of Alkyl Alcohol Using Sodium Hydroxide Solution 1121 g of the concentrated n-butanol solution produced in Example 6 (i.e. 49% w/w n-butanol) was charged to a 2 litre round bottomed flask fitted with a magnetic follower, 300 mm Vigreux column and a side-arm distillation assembly. The mixture was stirred at 300 rpm and 785 g of 3.2M sodium hydroxide solution was added dropwise from a dropping funnel and this mixture was then heated to boiling point (96° C.) at ambient pressure using an isomantle with an integral magnetic stirrer. Biphasic distillate was removed continuously and collected in a separating funnel. Phase separation was noted to occur quickly and the denser aqueous layer was drained from the separating funnel and a portion of this liquor (approximately one third by volume) was added back into the reactor from the top of the Vigreux column via a peristaltic pump until the distillate temperature reached 100° C. (reaction temperature 110° C.) and 1003.7 g of biphasic distillate had been removed. The mixture was cooled and discharged from the reactor yielding 902.3 g of a black coloured liquor and no visible solids. The liquor was tested for n-butanol content by Headspace-GC and found to contain just 0.12% w/w.

Example 8

Recovery of Solid Lignin From Residue 191.7 g of aqueous alkaline lignin solution arising from Example 7 and 797.2 g demineralised water were charged to a 1 litre glass beaker, fitted with an overhead stirrer and pH probe/thermocouple. The mixture was heated to c. 32° C. (where sodium sulfate is reported to reach a maximum solubility) with stirring at 300 rpm. 20.2 ml of 96% w/w sulphuric acid was added dropwise from a burette, with the pH of the mixture changing from 12.2 to 1.5. The acidified mixture was then vacuum filtered, producing a clear, amber coloured filtrate and a black solid. The solid filter cake was washed with 2×150 g and 1×115 g portion of demineralised water (at c. 32° C.). The "wet" filter cake (360 g) was dried to constant weight in an oven at 60° C. yielding 62 g of a black, free-flowing solid.

Example 9

Production of Butanol Solution of Lignin 9050 g of separated aqueous layer from Example 5 and 2881 g of a simulated n-butanol re-cycle stream (comprising of 72% w/w n-butanol, 21% w/w water, 4% w/w n-butyl acetate, and a number of other organic species) were charged to a jacketed 20 litre glass reactor equipped with a bottom drain valve. After mixing for 30 mins at 60° C., phase separation was performed by draining the denser aqueous layer from the bottom of the vessel. The remaining n-butanol solution of lignin and other components including n-butyl esters was finally transferred to a plastic drum and used as a co-feedstock for the following Examples.

Example 10

Recovery of Alkyl Alcohol Using a Simulated White Liquor Solution 958.5 g of an n-butanol solution containing lignin arising from Example 5 and 724.5 g of an n-butanol solution containing lignin arising from Example 9 were mixed together and 1672 g of the mixture were charged to a 2 litre jacketed glass reactor fitted with an overhead stirrer and a side-arm distillation assembly, and heated with oil supplied from a circulating bath. The mixture was stirred at 300 rpm and heated to boiling point (92.4° C.) at ambient pressure. A biphasic distillate was removed continuously until the temperature of the mixture reached 115° C. At this point 1005.5 g of the biphasic distillate was removed.

A sample of the partially concentrated n-butanol solution containing lignin was tested for n-butanol content by gas chromatography (GC) and found to be 59.6% w/w [i.e. 397 g n-butanol (59.6% of 666.5 g):269.5 g lignin and other components, e.g. n-butyl esters].

150 g of a simulated white liquor solution (comprising of 12.8% w/w sodium hydroxide, 4% w/w sodium sulphide and 83.2% w/w water) was charged to a 500 ml round bottomed flask fitted with a magnetic follower, 300 mm Vigreux column and a side-arm distillation assembly. The mixture was stirred at 300 rpm and 214 g of the partially concentrated n-butanol solution produced above (i.e. 59.6% w/w n-butanol) was added dropwise from a dropping funnel and this mixture was then heated to boiling point (97° C.) at ambient pressure using an electromantle with an integral magnetic stirrer. Biphasic distillate was removed continuously and collected in a separating funnel. Phase separation was noted to occur quickly and the denser aqueous layer was drained from the separating funnel and a portion of this liquor (approximately two thirds by volume) was added back into the reactor from the top of the Vigreux column via a peristaltic pump until the distillate temperature reached 100° C. (reaction temperature 110° C.). Total distillate take-off was maintained for a further 10 minutes and 184 g of biphasic distillate had been removed. The mixture was cooled and discharged from the reactor yielding 180 g of a black coloured liquor and no visible solids. The liquor was tested for n-butanol content by Headspace-GC and found to contain 0.86% w/w.

Example 11

Recovery of Alkyl Alcohol Using an Oxidised White Liquor Solution 941.5 g of an n-butanol solution containing lignin arising from Example 5 and 718.5 g of an n-butanol solution containing lignin arising from Example 9 were mixed together and 1637 g of the mixture were charged to a 2 litre jacketed glass reactor fitted with an overhead stirrer and a side-arm distillation assembly, and heated with oil supplied from a circulating bath. The mixture was stirred at 300 rpm and heated to boiling point (92.4° C.) at ambient pressure. A biphasic distillate was removed continuously until the temperature of the mixture reached 115° C. At this point 1005.5 g of the biphasic distillate was removed.

A sample of the partially concentrated n-butanol solution containing lignin was tested for n-butanol content by gas chromatography (GC) and found to be 67.2% w/w [i.e. 442 g n-butanol (67.2% of 657 g):215 g lignin and other components, e.g. n-butyl esters].

287 g of an oxidised white liquor solution from a Kraft dissolving pulp mill was charged to a 500 ml round bottomed flask fitted with a magnetic follower, 300 mm Vigreux column and a side-arm distillation assembly. The mixture was stirred at 300 rpm and 150 g of the concentrated n-butanol solution produced above (i.e. 67.2% w/w n-butanol) was added dropwise from a dropping funnel and this mixture was then heated to boiling point (97° C.) at ambient pressure using an electromantle with an integral magnetic stirrer. Biphasic distillate was removed continuously and collected in a separating funnel. Phase separation was noted to occur quickly and the denser aqueous layer was drained from the separating funnel and a portion of this liquor (approximately two thirds by volume) was added back into the reactor from the top of the Vigreux column via a peristaltic pump until the distillate temperature reached 100° C. Total distillate take-off was maintained for a further 30 minutes and 179.9 g of biphasic distillate had been removed. The mixture was cooled and discharged from the reactor yielding 257.1 g of a black coloured liquor and no visible solids. The liquor was tested for n-butanol content by Headspace-GC and found to contain 0.23% w/w.

The invention claimed is:

1. A method for processing an aqueous hemicellulosic stream containing lignin to provide an aqueous phase containing a monosaccharide derived from a hemicellulose of the hemicellulosic stream and a recovered $C_{3-8}$alkyl alcohol, the method comprising:
   (a) contacting the aqueous hemicellulosic stream containing lignin with a $C_{3-8}$alkyl alcohol at elevated temperature and acidic pH to provide a reaction mixture;
   (b) separating the reaction mixture obtained from (a) into an aqueous phase containing the monosaccharide and an organic phase containing the $C_{3-8}$alkyl alcohol;
   (c) concentrating the organic phase obtained from (b) by evaporation or distillation to remove and recover at least some of the $C_{3-8}$alkyl alcohol from the organic phase and to produce a concentrated residue comprising the $C_{3-8}$alkyl alcohol and $C_{3-8}$alkyl esters;
   (d) treating the concentrated residue from (c) with water or an aqueous medium having an alkaline pH to produce a mixture containing the $C_{3-8}$alkyl alcohol; and
   (e) recovering the $C_{3-8}$alkyl alcohol from the mixture containing the $C_{3-8}$alkyl alcohol of (d) by evaporation or distillation to produce recovered $C_{3-8}$alkyl alcohol and a further residue containing the lignin and products derived from the lignin.

2. The method of claim 1, wherein the $C_{3-8}$alkyl alcohol is n-butanol.

3. The method of claim 1, wherein (c) is carried out in a single stage or in at least two stages.

4. The method of claim 1, wherein the aqueous medium used in (d) has a pH of at least 10.

5. The method of claim 1, wherein:
   the aqueous hemicellulosic stream is an aqueous hemicellulosic stream having been produced in an industrial plant; and
   the aqueous medium used in (d) is an alkaline stream obtained from the same industrial plant as the aqueous hemicellulosic stream.

6. The method of claim 5, wherein the aqueous medium used in (d) is selected from the group consisting of black liquor, white liquor, green liquor, and mixtures thereof.

7. The method of claim 1, wherein the aqueous medium used in (d) is a sodium hydroxide solution.

8. The method of claim 1, wherein the concentrated residue in (d) is treated at a temperature from 90° C. to 130° C.

9. The method of claim 1, further comprising:
   (f) recycling the $C_{3-8}$alkyl alcohol recovered from (c) and/or (e) back to (a).

10. The method of claim 1, wherein the aqueous hemicellulosic stream is a hemicellulosic stream having been obtained from a process for producing dissolving pulp or from a process of treating biomass selected from the group consisting of treating the biomass with alkaline agents, treating the biomass with liquid ammonia, treating the biomass with alcohol, and treating the biomass with compressed liquid, hot water, or steam.

11. The method of claim 1, wherein the aqueous hemicellulosic stream is a pre-hydrolysis liquor having been obtained from a process for producing dissolving pulp.

12. The method of claim 1, wherein the aqueous hemicellulosic stream containing lignin and the $C_{3-8}$alkyl alcohol are contacted in (a) at from 130° C. to 170° C.

13. The method of claim 1, wherein the contacting at acidic pH in (a) is carried out in the presence of hydrochloric acid or sulfuric acid.

14. The method of claim 1, wherein (d) comprises treating the concentrated residue from (c) with an aqueous medium having an alkaline pH, the method further comprising:
   (k) treating with an acid at least part of the residue remaining after (e) to precipitate lignin.

15. The method of claim 1, further comprising:
   (g) reacting the monosaccharide obtained with the aqueous phase of (b) with a metal hydroxide or a quaternary ammonium hydroxide to produce a metal lactate or a quaternary ammonium lactate.

16. The method of claim 15, further comprising converting the metal lactate or quaternary ammonium lactate into alkyl lactate, oligomeric lactic acid, lactide, alkyl lactyllactate, polylactic acid, or a complex of lactic acid and either ammonia or an amine.

17. The method of claim 15, further comprising reacting at least a portion of the metal lactate or quaternary ammonium lactate with an acid to produce lactic acid.

18. The method of claim 17, further comprising converting the lactic acid into alkyl lactate, oligomeric lactic acid, lactide, alkyl lactyllactate, polylactic acid, or the complex.

19. The method of claim 1, wherein the monosaccharide comprises at least one of xylose, mannose, galactose, or glucose, the method further comprising one or both of (i) and (j):
  (i) converting the xylose into ethanol, n-butanol, i-butanol, lactic acid, xylitol, xylonic acid, itaconic acid, glutamic acid, proline, ethylene glycol, propylene glycol, and/or furfural; and
  (j) converting the mannose, galactose, or glucose into ethanol, n-butanol, i-butanol, lactic acid, succinic acid, acrylic acid, sorbitol, ethylene glycol, propylene glycol, and/or 5-hydroxymethylfurfural.

20. The method of claim 1, further comprising converting the monosaccharide obtained from the aqueous phase of (b) into ethanol, n-butanol, i-butanol, lactic acid, xylitol, xylonic acid, itaconic acid, glutamic acid, proline, ethylene glycol, propylene glycol, furfural, succinic acid, acrylic acid, sorbitol, or 5-hydroxymethylfurfural.

* * * * *